US00PP22557P2

(12) United States Plant Patent

Miedema-Jorna

(10) Patent No.: US PP22,557 P2

(45) Date of Patent: Mar. 6, 2012

(54) **GUINEA *IMPATIENS* PLANT NAMED 'FIDIMPREDBICO'**

(50) Latin Name: *Impatiens hawkeri*
Varietal Denomination: Fidimpredbico

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/806,255

(22) Filed: Aug. 7, 2010

(51) Int. Cl.
*A01H 5/00* (2006.01)

(52) U.S. Cl. ..... Plt./318.1

(58) Field of Classification Search ..... Plt./318.1
See application file for complete search history.

*Primary Examiner* — Susan McCormick Ewoldt

(74) *Attorney, Agent, or Firm* — C. A. Whealy

(57) ABSTRACT

A new and distinct cultivar of *Impatiens* plant named 'Fidimpredbico' characterized by its upright and outwardly spreading growth habit; mounded plant form; freely branching habit; dark green-colored leaves; freely flowering habit; large orange red and light red bi-colored flowers; and good garden performance.

1 Drawing Sheet

Botanical designation: *Impatiens hawkeri.*
Cultivar denomination: 'FIDIMPREDBICO'.

BACKGROUND OF THE INVENTION

The present invention relates to a new and distinct cultivar of New Guinea *Impatiens* plant, botanically known as *Impatiens hawkeri* and hereinafter referred to by the name 'Fidimpredbico'.

The new *Impatiens* plant is a product of a planned breeding program conducted by the Inventor in De Lier, The Netherlands. The objective of the breeding program is to create new freely-branching New Guinea *Impatiens* plants with freely flowering habit and large attractive flowers.

The new *Impatiens* plant originated from a cross-pollination made in 2006 by the Inventor in De Lier, The Netherlands of an unnamed proprietary selection of *Impatiens hawkeri*, not patented, as the female, or seed, parent with a proprietary selection of *Impatiens hawkeri* identified as code number AMI 1011, not patented, as the male, or pollen, parent. The new *Impatiens* plant was discovered and selected by the Inventor as a single flowering plant within the progeny of the stated cross-pollination in a controlled environment in De Lier, The Netherlands.

Asexual reproduction of the new *Impatiens* plant by vegetative cuttings in a controlled environment in De Lier, The Netherlands since 2008, has shown that the unique features of this new *Impatiens* plant are stable and reproduced true to type in successive generations.

SUMMARY OF THE INVENTION

Plants of the new *Impatiens* plant have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fidimpredbico' . These characteristics in combination distinguish 'Fidimpredbico' as a new and distinct cultivar of *Impatiens* plant:

1. Upright and outwardly spreading growth habit; mounded plant form.
2. Freely branching habit.
3. Dark green-colored leaves.
4. Freely flowering habit.
5. Large orange red and light red bi-colored flowers.
6. Good garden performance.

Plants of the new *Impatiens* can be compared to plants of the female parent selection. Plants of the new *Impatiens* differ from plants of the female parent selection in the following characteristics:

1. Plants of the new *Impatiens* had slightly larger flowers than plants of the female parent selection.
2. Flowers of plants of the new *Impatiens* and the female parent selection differ in flower color.

Plants of the new *Impatiens* can be compared to plants of the male parent selection. Plants of the new *Impatiens* differ from plants of the male parent selection in the following characteristics:

1. Plants of the new *Impatiens* are more freely branching than plants of the male parent selection.
2. Plants of the new *Impatiens* do not stretch whereas plants of the male parent selection stretch.

Plants of the new *Impatiens* can be compared to plants of *Impatiens* 'Tamar Red Bicolor', disclosed in U.S. Plant Pat. No. 17,966. In side-by-side comparisons conducted in De Lier, The Netherlands, plants of the new *Impatiens* differed from plants of 'Tamar Red Bicolor' in the following characteristics:

1. Plants of the new *Impatiens* were more vigorous than plants of 'Tamar Red Bicolor'.
2. Flowers of plants of the new *Impatiens* were darker orange red in color than plants of 'Tamar Red Bicolor'.

BRIEF DESCRIPTION OF THE PHOTOGRAPH

The accompanying colored photograph illustrates the overall appearance of the new *Impatiens* plant, showing the colors as true as it is reasonably possible to obtain in colored reproductions of this type. Colors in the photograph may differ slightly from the color values cited in the detailed botanical description which accurately describe the colors of the new *Impatiens* plant. The photograph comprises a top perspective view of a typical flowering plant of 'Fidimpredbico' grown in a container.

DETAILED BOTANICAL DESCRIPTION

The aforementioned photograph and following observations, measurements and values describe plants grown in 12-cm containers in a glass-covered greenhouse in De Lier, The Netherlands under commercial practice with day and night temperatures averaging 18° C. Plants were nine weeks old when the photograph and description were taken. In the following description, color references are made to The Royal Horticultural Society Colour Chart, 2001 Edition, except where general terms of ordinary dictionary significance are used.

Botanical classification: *Impatiens hawkeri* 'Fidimpredbico'.

Parentage:

*Female, or seed, parent.*—Unnamed proprietary selection of *Impatiens hawkeri*, not patented.

*Male, or pollen, parent.*—Proprietary selection of *Impatiens hawkeri* identified as code number AMI 1011, not patented.

Propagation:

*Type.*—By vegetative cuttings.

*Time to initiate roots, summer.*—About five to seven days at temperatures of 19° C. to 20° C.

*Time to initiate roots, winter.*—About six to eight days at temperatures of 19° C. to 20° C.

*Time to produce a rooted young plant, summer.*—About 14 to 19 days at temperatures of 19° C. to 20° C.

*Time to produce a rooted young plant, winter.*—About 14 to 21 days at temperatures of 19° C. to 20° C.

*Root description.*—Fine; white to brown in color.

*Rooting habit.*—Freely branching.

Plant description:

*Plant and growth habit.*—Upright and outwardly spreading growth habit; mounded plant form; freely branching habit with about eight lateral branches; pinching is typically not required; moderately vigorous growth habit.

*Plant height.*—About 22 cm.

*Plant diameter.*—About 38 cm.

Lateral branch description:

*Length.*—About 8 cm.

*Diameter.*—About 6 mm.

*Internode length.*—About 3 cm.

*Strength.*—Moderately strong.

*Aspect.*—Initially upright to outwardly spreading.

*Texture.*—Smooth, glabrous.

*Color.*—Close to 146C; at the nodes, tinted with close to 184A.

Foliage description:

*Arrangement.*—Opposite or in whorls of about five; simple.

*Length.*—About 10.5 cm.

*Width.*—About 4 cm.

*Shape.*—Elliptic.

*Apex.*—Acute.

*Base.*—Attenuate.

*Margin.*—Serrate with ciliation.

*Texture, upper and lower surfaces.*—Smooth, glabrous; leathery; moderately glossy in luster.

*Venation pattern.*—Pinnate; arcuate.

*Color.*—Developing leaves, upper surface: Close to N137A. Developing leaves, lower surface: Darker than 183A. Fully expanded leaves, upper surface: Darker than 147A; venation, close to 183A. Fully expanded leaves, lower surface: Close to 147B tinted with close to 183A; venation, close to 183A.

*Petiole.*—Length: About 3 cm. Diameter: About 3 mm. Texture, upper and lower surfaces: Smooth, glabrous. Color, upper and lower surfaces: Center, close to 182C; towards the edges, close to 183A.

Flower description:

*Flower type and flowering habit.*—Single rounded axillary flowers; freely flowering habit with about 15 flowers developing per lateral branch; flowers positioned above the foliage and typically face upright or outwardly.

*Fragrance.*—None detected.

*Natural flowering season.*—Year-round under greenhouse conditions; in the garden, continuous flowering from spring through the summer in The Netherlands; early flowering habit, plants begin flowering about nine weeks after planting.

*Flower longevity.*—Flowers last about ten days on the plant under greenhouse conditions; petals self-cleaning, gynoecium persistent.

*Flower size.*—Diameter: About 6.5 cm. Depth: About 1 cm.

*Flower buds.*—Length: About 2 cm. Diameter: About 1 cm. Shape: Ovoid; pointed. Color: Close to 185A, 41B and 38A; stripe, close to N186C.

*Petals.*—Quantity/arrangement: Five per flower in a single whorl. Length, banner petal: About 3 cm. Length, lateral and lower petals: About 4.2 cm. Width, banner petal: About 5.8 cm. Width, lateral and lower petals: About 3 cm. Shape, banner petal: Cordate. Shape, lateral and lower petals: Broadly cordate. Apex, banner petal: Mucronate. Apex, lateral and lower petals: Emarginate. Base, all petals: Attenuate. Margin, all petals: Entire. Texture, all petals, upper and lower surfaces: Smooth, glabrous. Color, banner petal: When opening and fully opened, upper surface: Center, close to N30A; towards the margins, close to 56A; towards the base, close to 58B; color does not fade with development. When opening and fully opened, lower surface: Center, close to 46A; grading towards the margins, from 58B to 41B to 41C; central stripe, close to N186C. Color, lateral and lower petals: When opening and fully opened, upper surface: Center, close to N30A to N30B; towards the margins, close to 56A; towards the base, close to 58B; color does not fade with development. When opening and fully opened, lower surface: Center, close to 41B; grading towards the margins, close to 41C to 56A.

*Sepals.*—Quantity/arrangement: Three; one modified into an elongated spur. Length, spurred sepal: About 1.4 cm. Length, spur: About 4.4 cm. Length, lateral sepals: About 1.2 cm. Width, spurred sepal: About 1.6 cm. Diameter, spur: About 1.5 mm. Width, lateral sepals: About 6 mm. Shape, spurred sepal: Broadly ovate with elongate spur. Shape, lateral sepals: Ovate. Apex, all sepals: Apiculate. Base, all sepals: Cuneate. Margin, all sepals: Entire. Texture, all sepals, upper and lower surfaces: Smooth, glabrous. Color, spurred sepal: Upper surface: Towards the base, close to 56D; towards the apex, close to 139D tinted with close to 55B. Lower surface: Center, close to 54B and 60B; towards the margins, close to 59D; towards the apex, close to N186C. Spur, upper and lower surfaces: Close to 145B to 145C. Color, lateral sepals: Upper surface: Close to 139D tinted with close to N186C; towards the margins, close to 59C. Lower surface: Center, close to 59C to 59D; towards the apex, close to 186C.

*Peduncles.*—Length: About 4 cm. Diameter: About 2 mm. Angle: Mostly erect. Strength: Moderately strong. Texture: Smooth, glabrous. Color: Close to 145B to 145C.

*Reproductive organs.*—Stamens: Quantity: Five fused at anthers; filaments free. Anther length: About 2 mm. Anther color: Close to 180A and 185A. Pollen amount: Scarce. Pollen color: Close to N155A. Pistils: Quantity per flower: One. Pistil length: About 0.5 mm. Stigma shape: Capitate. Stigma color: Close to 187C. Ovary color: Close to 144C tinted with close to 185A.

*Seed/fruit.*—Seed and fruit production have not been observed.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate wind, rain and temperatures ranging from about 4° C. to about 35° C.

It is claimed:

1. A new and distinct *Impatiens* plant named 'Fidimpredbico' as illustrated and described.

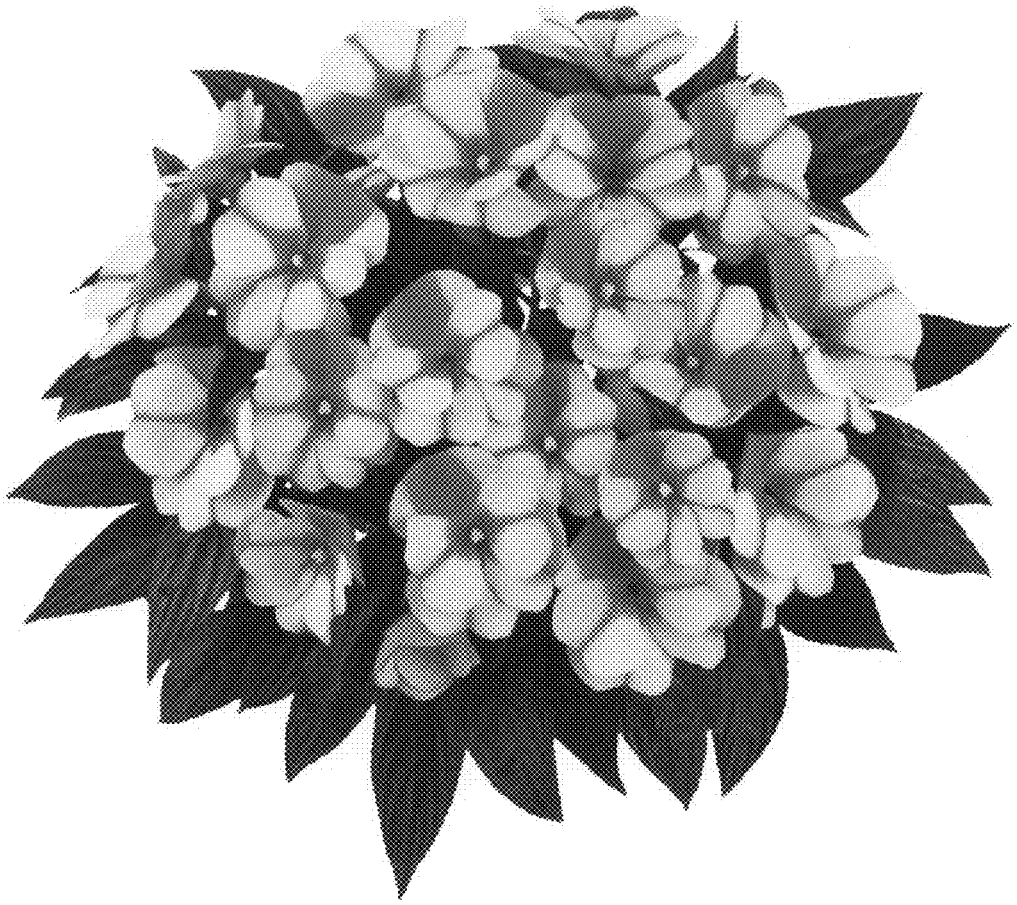

* * * * *